United States Patent
Rao et al.

(10) Patent No.: US 10,287,248 B2
(45) Date of Patent: May 14, 2019

(54) PROCESS FOR THE PREPARATION OF APREMILAST

(71) Applicant: Cipla Limited, Mumbai (IN)

(72) Inventors: Dharmaraj Ramachandra Rao, Mumbai (IN); Geena Malhotra, Mumbai (IN); Srinivas Laxminarayan Pathi, Bangalore (IN); Ravikumar Puppala, Bangalore (IN); Suryanarayana Durga Yarra, Bangalore (IN)

(73) Assignee: CIPLA LIMITED, Mumbai (IN)

( * ) Notice: Subject to any disclaimer, the term of this patent is extended or adjusted under 35 U.S.C. 154(b) by 0 days.

(21) Appl. No.: 15/554,602

(22) PCT Filed: Mar. 15, 2016

(86) PCT No.: PCT/GB2016/050699
§ 371 (c)(1),
(2) Date: Aug. 30, 2017

(87) PCT Pub. No.: WO2016/146990
PCT Pub. Date: Sep. 22, 2016

(65) Prior Publication Data
US 2018/0237390 A1      Aug. 23, 2018

(30) Foreign Application Priority Data
Mar. 19, 2015 (IN) .......................... 913/MUM/2015

(51) Int. Cl.
C07D 209/48 (2006.01)
(52) U.S. Cl.
CPC .................. C07D 209/48 (2013.01)
(58) Field of Classification Search
CPC .................................................. C07D 209/48
USPC ......................................................... 548/478
See application file for complete search history.

(56) References Cited

U.S. PATENT DOCUMENTS

| 6,667,316 | B1 * | 12/2003 | Man ................... C07D 209/46 514/323 |
| 8,455,536 | B2 | 6/2013 | Muller et al. |
| 2006/0183787 | A1 * | 8/2006 | Muller ............... A61K 31/4035 514/417 |
| 2006/0183788 | A1 * | 8/2006 | Muller ............... A61K 31/4035 514/417 |
| 2012/0178708 | A1 | 7/2012 | Kumar et al. |

FOREIGN PATENT DOCUMENTS

| WO | 2009120167 A1 | 10/2009 |
| WO | 2012083153 A1 | 6/2012 |
| WO | 2014151180 A1 | 9/2014 |

OTHER PUBLICATIONS

Man et al. J. Med. Chem. 52, 1522-1524 (Year: 2009).*
Office Action dated Sep. 10, 2018 for the corresponding European Patent Application No. 16 713 561.5.

* cited by examiner

*Primary Examiner* — Nyeemah A Grazier
(74) *Attorney, Agent, or Firm* — Rankin, Hill & Clark LLP

(57) ABSTRACT

The present invention relates to novel processes for the preparation of apremilast of formula I, or a pharmaceutically acceptable salt thereof.

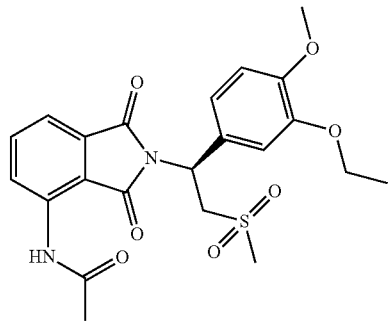

Formula I

30 Claims, No Drawings

PROCESS FOR THE PREPARATION OF APREMILAST

FIELD OF THE INVENTION

The present invention relates to improved, commercially viable and industrially advantageous processes for the preparation of apremilast (a compound of formula I) or a pharmaceutically acceptable salt thereof.

BACKGROUND OF THE INVENTION

Apremilast is an orally available small molecule inhibitor of phosphodiesterase (PDE4). Apremilast specifically inhibits PDE4 and inhibits spontaneous production of TNF-alpha from human rheumatoid synovial cells. It has anti-inflammatory activity.

Apremilast, chemically termed as N-[2-[(1S)-1-(3-ethoxy-4-methoxyphenyl)-2-(methylsulfonyl) ethyl]-2,3-dihydro-1,3-dioxo-1H-isoindol-4-yl]acetamide has the following structural Formula I.

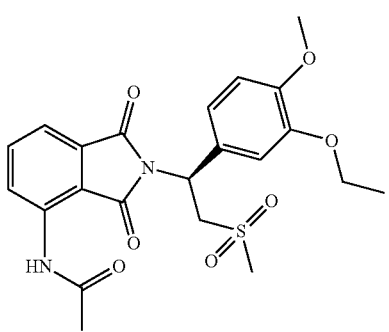

Formula I

EP1752148 (B1) discloses a process for the preparation of a racemic mixture of 2-[1-(3-ethoxy-4-methoxyphenyl)-2-methylsulfonylethyl]-4-acetamidoisoindoline-1,3-dione which comprises reacting 1-(3-ethoxy-4-methoxyphenyl)-2-methylsulfonylethyl amine with 3-acetamidophthalic anhydride in acetic acid at reflux for 15 hours.

Several other approaches are also described in the literature to prepare apremilast.

U.S. Pat. No. 8,455,536 B2 (hereinafter referred to as the '536 patent) provides a process for the preparation of apremilast, wherein the process involves the steps of:
a) reducing 3-nitrophthalic acid using 10% Pd/C in a Parr hydrogenator with H$_2$ up to 55 psi for 13 hours to obtain 3-aminopthalic acid;
b) reacting 3-aminopthalic acid with acetic anhydride at reflux temperature for 3 hours to obtain 3-acetamidophthalic anhydride;
c) resolution of racemic 2-(3-ethoxy-4-methoxyphenyl)-1-(methylsulphonyl)-eth-2-ylamine using N-acetyl-L-leucine in methanol at reflux for 1 hour to obtain (S)-2-(3-ethoxy-4-methoxy phenyl)-1-(methylsulphonyl)-eth-2-yl amine N-acetyl-L-leucine salt; and
d) reacting overnight the N-acetyl-L-leucine salt of (S)-2-(3-ethoxy-4-methoxyphenyl)-1-(methylsulphonyl)-eth-2-yl amine with 3-acetamidophthalic anhydride in 10 volume glacial acetic acid, at reflux temperature for 15 hours to obtain apremilast in 75% yield.

CN103864670 discloses the preparation of apremilast by condensing 1-[(R)-amino(phenyl)methyl]-2-naphthol with 3-ethoxy-4-methoxybenzaldehyde in the presence of triethyl amine in methanol to yield the naphtho[1,2-e][1,3]oxazine derivative, which upon addition of dimethylsulfone lithium salt in tetrahydrofuran gives N-[(2S)-(1-(3-ethyoxyl-4-methoxyphenyl)-2-methylsulfonylethyl)]-(1R)-(α-aminobenzyl)-2-iso naphthol which undergoes hydrogenation over Pd/C in methanol to yield 1(S)-(3-ethoxy-4-methoxyphenyl)-2-(methylsulfonyl)ethylamine, which is finally condensed with 3-acetamidophthalic anhydride in refluxing glacial acetic acid for 24 hours.

WO2012083153 A1 discloses the preparation of apremilast by acetylating (S)-4-amino-2-(1-(3-ethoxy-4-methoxyphenyl)-2-(methylsulfonyl) ethyl) isoindoline-1,3-dione (2-[(1S)-1-(3-ethoxy-4-methoxyphenyl)-2-(methyl sulfonyl) ethyl]-4-aminoisoindoline-1,3-dione) with acetic anhydride and acetic acid at 125° C. for 30 minutes.

The prior art processes disclosed above involve the use of acetic anhydride and a large quantity of solvents which are not safe for handling and are also environmental pollutants. As such, these processes are considered hazardous, complex and difficult to carry out.

Therefore, there exists a need for a more economical and efficient method of making apremilast which is suitable for industrial scale-up.

OBJECTS OF THE INVENTION

An object of the present invention is to provide an alternative and improved process for the preparation of apremilast (a compound of formula I) or a pharmaceutically acceptable salt thereof.

Another object of the present invention is to provide an improved process for the preparation of compound of formula II.

Yet another object of the present invention is to provide a process for the preparation of apremilast (of formula I) or a pharmaceutically acceptable salt thereof which is simple, economical and easy to handle at an industrial scale and commercially viable.

SUMMARY OF THE INVENTION

The present invention relates to processes for the preparation of apremilast or a pharmaceutically acceptable salt thereof, which are simple, cost effective, eco-friendly, commercially suitable and non-hazardous and industrially scalable.

According to a first aspect of the invention, there is provided a process for preparing apremilast of formula I, or a pharmaceutically acceptable salt thereof,

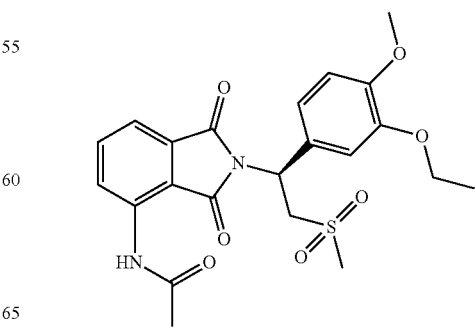

Formula I which process comprises acetylating (S)-4-amino-2-(1-(3-ethoxy-4-methoxyphenyl)-2-(methylsulfonyl) ethyl) isoindoline-1,3-dione (2-[(1 S)-1-(3-ethoxy-4-methoxyphenyl)-2-(methyl sulfonyl)ethyl]-4-aminoisoindoline-1,3-dione)) of formula II

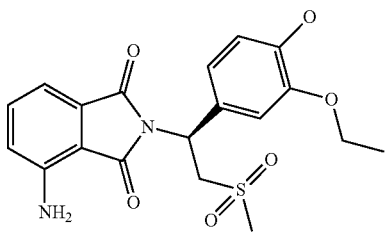

II with an acetylating agent in the presence of a base to obtain apremilast of formula I; and optionally thereafter forming a pharmaceutically acceptable salt of the compound so formed.

According to a second aspect of the present invention, there is provided a process for preparing apremilast of formula I, or a pharmaceutically acceptable salt thereof, which process comprises the steps of (a) protonating and cyclizing a salt of (S)-1-(3-ethoxy-4-methoxyphenyl)-2-(methylsulfonyl)ethanamine of formula III

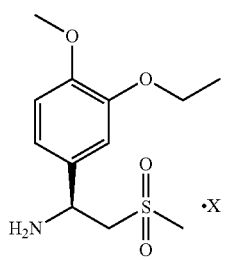

III with 3-amino phthalic acid in the presence of a protonating agent to obtain (S)-4-amino-2-(1-(3-ethoxy-4-methoxyphenyl)-2-(methylsulfonyl) ethyl) isoindoline-1,3-dione of formula II;

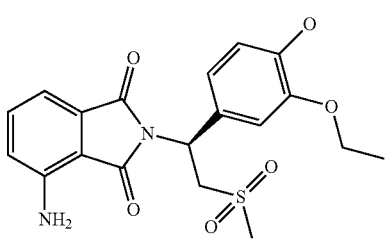

II and (b) acetylating (S)-4-amino-2-(1-(3-ethoxy-4-methoxyphenyl)-2-(methylsulfonyl) ethyl) isoindoline-1,3-dione of formula II with an acetylating agent in the presence of a base to obtain apremilast of formula I, and optionally thereafter forming a pharmaceutically acceptable salt of the compound so formed; wherein there is no isolation of (S)-4-amino-2-(1-(3-ethoxy-4-methoxyphenyl)-2-(methylsulfonyl) ethyl) isoindoline-1,3-dione of formula II between steps (a) and (b).

The prior art suggests the reaction of 3-amino phthalic acid with acetic anhydride at 140° C. to obtain 3-acetamidophthalic anhydride which is further reacted with (S)-1-(3-ethoxy-4-methoxy phenyl)-2-(methylsulfonyl) ethanamine leucine salt in acetic acid to form apremilast.

As such, the processes described in the prior art require heating of acetic anhydride with 3-amino phthalic acid at high temperatures.

The acetic anhydride used in the process is an irritant and a combustible liquid. Further, acetic anhydride is used as a precursor in the manufacturing of illicit narcotic drugs and psychotropic substances. Hence when used in commercial processes strict records of the quantities consumed are required. As such, the commercial handling of acetic anhydride on a bulk scale is difficult and requires very complex logistics.

The present invention provides a simplified process wherein a salt of (S)-1-(3-ethoxy-4-methoxyphenyl)-2-(methylsulfonyl) ethanamine of formula III is condensed with 3-amino phthalic acid. The simplified process avoids the preparation of a 3-acetamido phthalic anhydride intermediate and hence avoids the use of acetic anhydride as disclosed in the prior art ('536 patent). This may be considered one advantage of the present invention.

A further advantage of the condensation reaction of the present invention is that the reaction time may be reduced drastically from the 15 hours disclosed in the prior art down to about 3-4 hours. This may be considered a second advantage of the present invention.

Further, the temperature of the condensation reaction may be performed at lower temperatures than analogous reactions reported in the prior art (for example in one case, the temperature may be reduced from the 118° C. disclosed in the prior art down to about 80° C.). This may be considered a third advantage of the present invention.

Further, the condensation reaction may be carried out in about 1 volume to about 2 volumes of acetic acid instead of 10 volumes of acetic acid as reported in the prior art. This thus avoids the handling of a large quantity of acetic acid on the industrial scale. This may be considered a fourth advantage of the present invention.

The use of lower volumes of acetic acid at lower temperatures and at reduced reaction volumes and times will reduce the overall cost of production, simplifies work up and minimizes the effluent disposal problem. This may be considered a fifth advantage of the present invention.

Further, the acetylation reaction of the present invention is preferably carried out with acetyl chloride. This process avoids the use of acetic anhydride and acetic acid as reported in WO2012083153 A1. In the present invention, the reaction may be carried out at a lower temperature as compared to this prior art process which is carried out at 125° C. This may be considered a sixth advantage of the present invention.

According to a third aspect of the invention, there is provided apremilast or a pharmaceutically acceptable salt thereof prepared by a process of the present invention as described herein.

According to a fourth aspect of the present invention, there is provided a pharmaceutical composition comprising apremilast or a pharmaceutically acceptable salt thereof, prepared by a process of the present invention as described herein, together with one or more pharmaceutically acceptable excipients.

According to a fifth aspect of the present invention, there is also provided apremilast, or a pharmaceutically acceptable salt thereof prepared by a process of the present invention as described herein for use in the treatment of psoriasis or psoriatic arthritis.

According to a sixth aspect of the invention, there is provided a process for preparing (S)-4-amino-2-(1-(3-ethoxy-4-methoxyphenyl)-2-(methylsulfonyl) ethyl) isoindoline-1,3-dione of formula II

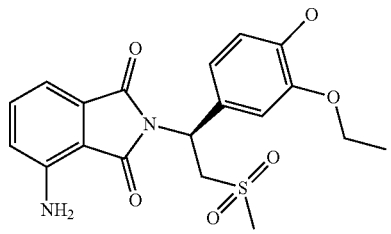

which process comprises protonating and cyclizing a salt of (S)-1-(3-ethoxy-4-methoxyphenyl)-2-(methylsulfonyl) ethanamine of formula III

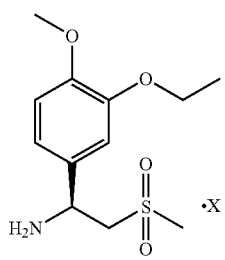

with 3-amino phthalic acid in the presence of a protonating agent.

DETAILED DESCRIPTION OF THE INVENTION

The processes of the present invention avoid the use of reagents such as acetic anhydride, avoid using a large quantity of acetic acid and allow a substantial reduction in a number of problems associated with these reagents. There is also a considerable reduction in the reaction time and temperature.

Provided herein is a novel and improved process for preparing apremilast of formula I or a pharmaceutically acceptable salt thereof.

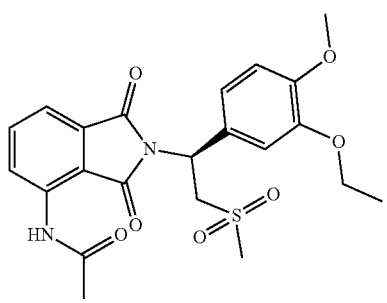

Formula I

According to a first aspect of the present invention, the process comprises the steps of: Step (i) optionally reacting 1-(3-ethoxy-4-methoxyphenyl)-2-(methylsulfonyl)ethanamine of formula IV;

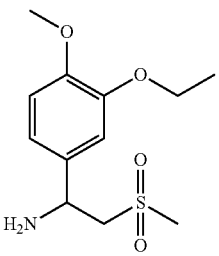

with a chiral resolving agent and isolating a salt of (S)-1-(3-ethoxy-4-methoxyphenyl)-2-(methylsulfonyl)ethanamine of formula III;

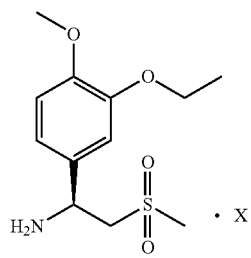

Step (ii) optionally protonating and cyclizing the salt of (S)-1-(3-ethoxy-4-methoxyphenyl)-2-(methylsulfonyl) ethanamine of formula III with 3-amino phthalic acid in the presence of a protonating agent, preferably in the presence of a suitable base and a suitable organic solvent at a suitable temperature, yielding 2-[(1S)-1-(3-ethoxy-4-methoxyphenyl)-2-(methyl sulfonyl)ethyl]-4-aminoisoindoline-1,3-dione of formula II;

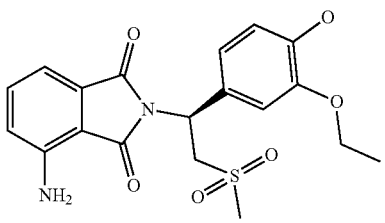

Step (iii) acetylating 2-[(1S)-1-(3-ethoxy-4-methoxyphenyl)-2-(methylsulfonyl)ethyl]-4-aminoisoindoline-1,3-dione of formula II with an acetylating agent in the presence of a base to obtain apremilast of formula I; and optionally thereafter converting the compound of formula I to a pharmaceutically acceptable salt thereof.

In an embodiment of the present invention, there is provided a process for the preparation of apremilast, or a pharmaceutically acceptable salt thereof, as depicted below in reaction scheme I.

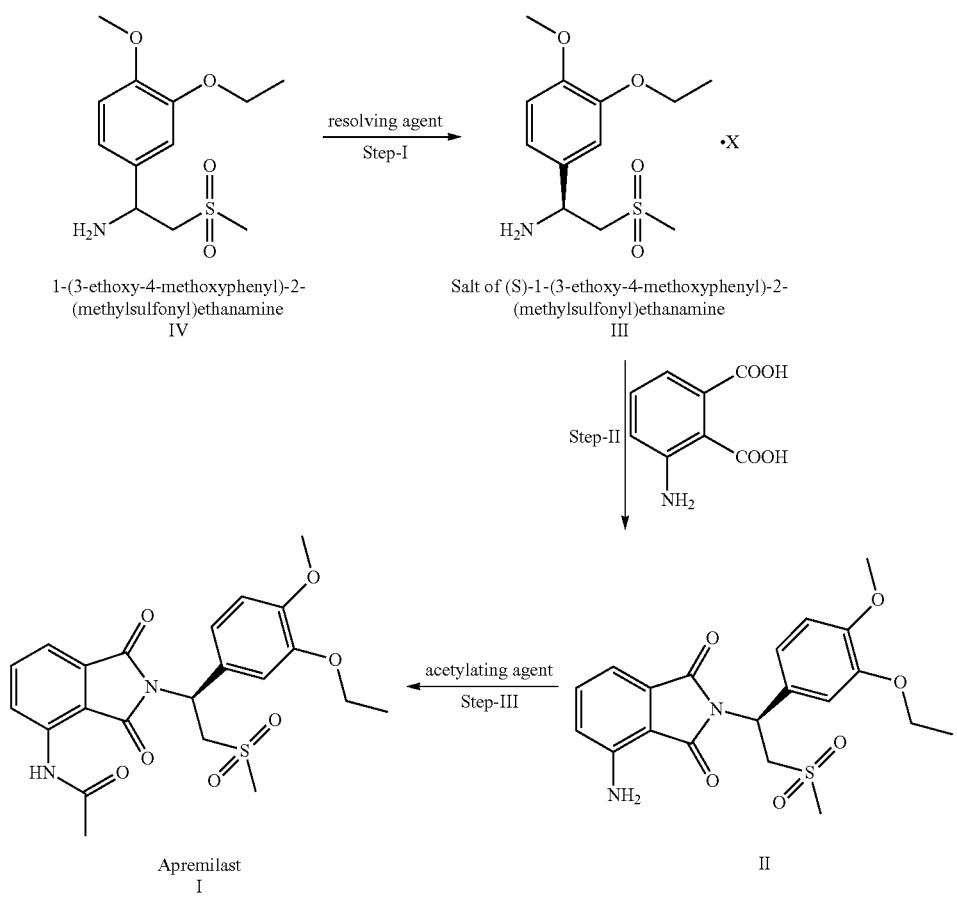

Scheme-I 1-(3-ethoxy-4-methoxyphenyl)-2-(methylsulfonyl)ethanamine
IV

Salt of (S)-1-(3-ethoxy-4-methoxyphenyl)-2-(methylsulfonyl)ethanamine
III

Apremilast
I

II

The term "X" used herein is understood to mean salt.

The term "salt", used herein, denotes an acidic salt formed with chiral resolving agents.

The term "chiral resolving agent" used herein is understood to mean an agent that can be used for resolving enantiomers.

As used herein and unless otherwise indicated, the term "pharmaceutically acceptable salt" includes, but is not limited to, salts prepared from pharmaceutically acceptable acids or bases including organic acids and bases and inorganic acids and bases. Suitable salts include, but are not limited to, those derived from organic and inorganic acids such as hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

As depicted in step I, 1-(3-ethoxy-4-methoxyphenyl)-2-(methylsulfonyl) ethanamine (IV) is reacted with a suitable chiral resolving agent, preferably in a suitable solvent (or mixture of solvents thereof) preferably at a suitable temperature for a suitable time (for example 1-2 hours) to form a salt of (S)-1-(3-ethoxy-4-methoxyphenyl)-2-(methylsulfonyl)ethanamine (Ill), preferably the N-acetyl-L-leucine salt.

Suitable chiral resolving agents for use in the present invention include, but are not limited to, tartaric acids such as tartaric acid, di-benzoyl tartaric acid, di-p-toluoyl tartaric acid, o-nitrobenzoyl tartaric acid, diacetyltartaric acidand the like; camphorsulphonic acids such as 10-camphorsulphonic acid, 8-camphorsulphonic acid and the like; malic acids, N-acetyl glutamic acids, mandelic acids and the like; chiral amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, N-acetyl-L-leucine, 10-camphor sulfonic acid, camphoric acid, α-bromocamphoric acid, methoxyacetic acid and the like. Preferably the chiral resolving agent is a chiral amino acid, more preferably N-acetyl-L-leucine.

Suitable organic solvents for use in the present invention include, but are not limited to, alcohols such as methanol, ethanol, isopropanol, butanol and the like; ketones such as acetone, methyl ethyl ketone, methyl isobutyl ketone, and the like; halogenated solvents such as dichloroethane, dichloromethane, chloroform and the like; esters such as ethyl acetate, isopropyl acetate, n-propyl acetate and the like; nitriles such as acetonitrile, propionitrile and the like; hydrocarbons such as toluene, xylene, cyclohexane, heptane, xylene and the like; and mixtures thereof in various proportion without limitation. Preferably the organic solvent is an alcohol, more preferably methanol.

Suitable temperatures for conducting the step I reaction range from about 0° C. to about reflux temperature of the solvent used. Preferably the reaction mixture is heated to about reflux.

As depicted in step II the process comprises protonating and cyclizing the salt of (S)-1-(3-ethoxy-4-methoxyphenyl)-2-methanesulfonylethylamine (Ill) with 3-amino phthalic acid in the presence of a protonating agent and preferably in the presence of a suitable base and/or a suitable organic solvent, preferably at a suitable temperature, to form the compound of formula (II).

Step II may further comprise isolating and drying the compound of formula (II) into a solid form. Any suitable techniques known in the art may be used, for example filtering and then drying under vacuum.

Suitable protonating agents are proton-yielding compounds such as mineral acids such as hydrochloric acid, sulphuric acid, phosphoric acid; sulphonic acids such as p-toluenesulphonic acid; carboxylic acids (e.g. alkanecarboxylic acids such as acetic acid or aromatic carboxylic acid); alcohols (for example, alkanols such as methanol, ethanol); phenols; amines and ammonium compounds having at least one available hydrogen atom, for example, ammonia (liquid or gaseous), primary or secondary amines such as mono or dialkyl amines, ammonium halides (e.g. chlorides or bromides; solid or as aqueous solution), pyridine hydrohalides; water and the like. Preferably the protonating agent is a carboxylic acid, more preferably an alkane carboxylic acid, most preferably acetic acid.

Suitable organic solvents include, but are not limited, to dimethylsulfoxide (DMSO), N,N-dimethylformamide (DMF), N,N-dimethylacetamide (DMA), tetrahydrofuran, acetone, acetonitrile, toluene and the like or mixtures thereof in various proportions. Preferably the organic solvent is acetonitrile.

Suitable bases include, but are not limited to, organic bases such as methylamine, dimethylamine, triethylamine and the like; and inorganic bases such as sodium hydroxide, potassium hydroxide, sodium carbonate, potassium carbonate, sodium bicarbonate, potassium bicarbonate, sodium methoxide, potassium methoxide and the like. Preferably the base is an organic base, more preferably it is triethylamine.

Suitable temperatures for conducting the step II reaction range from about 10° C. to about 90° C., preferably from about 25° C. to about 80° C., about 50° C. to about 80° C. about 70° C. to about 80° C., or most preferably about 80° C.

As depicted in step III, the process comprises acetylating (S)-4-amino-2-(1-(3-ethoxy-4-methoxyphenyl)-2-(methylsulfonyl)ethyl)isoindoline-1,3-dione (II) with an acetylation agent in the presence of a base preferably in a suitable solvent to obtain apremilast.

Step III may further comprise isolating and drying apremilast into a solid form. Any suitable techniques known in the art may be used, for example filtering and then drying under vacuum.

The acetylation agent may be selected from, but not limited to, acetyl chloride, acetic acid or mixtures thereof. Preferably the acetylation agent is acetyl chloride.

The base used for acetylation may be selected from an inorganic or organic base.

Preferably the inorganic base is selected from the group consisting of sodium bicarbonate, potassium bicarbonate, lithium carbonate, sodium carbonate, potassium carbonate, sodium hydroxide, potassium hydroxide or any mixture thereof and the organic base is selected from the group consisting of diisopropylamine, diisopropylethylamine triethylamine, dimethylamine, trimethyl amine, pyridine or any mixtures thereof. Preferably the base for acetylation is an inorganic base, more preferably an inorganic carbonate, most preferably potassium carbonate.

A suitable solvent for the acetylation reaction is selected from the group consisting of aromatic hydrocarbons, chlorinated hydrocarbons and esters. Suitable examples of aromatic hydrocarbons include, but are not limited to, toluene, xylene, benzene and the like or a mixture thereof. Suitable examples of chlorinated hydrocarbons include, but are not limited to, dichloromethane, dichloroethane, chloroform, carbon tetrachloride and the like or any mixture thereof. Suitable examples of esters include, but are not limited to, ethyl acetate, butyl acetate, isopropyl acetate and the like or a mixture thereof. Preferably the solvent is an ester, more preferably ethyl acetate.

Suitable temperatures for the acetylation reaction are room temperature, i.e. about 20-30° C., most preferably 25-30° C.

According to a second aspect of the present invention, there is provided a process for the preparation of apremilast without isolation of intermediates (preferably intermediate of formula (II)).

In an embodiment, there is provided a process for the preparation of apremilast of formula I without isolation of intermediates (also referred to as "in one pot" and other related variations) as depicted in Scheme II.

Scheme II

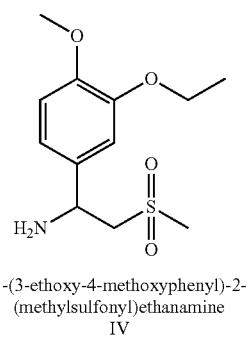

1-(3-ethoxy-4-methoxyphenyl)-2-(methylsulfonyl)ethanamine
IV

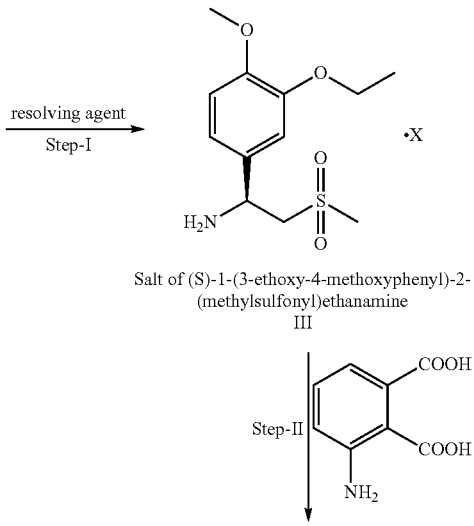

Salt of (S)-1-(3-ethoxy-4-methoxyphenyl)-2-(methylsulfonyl)ethanamine
III

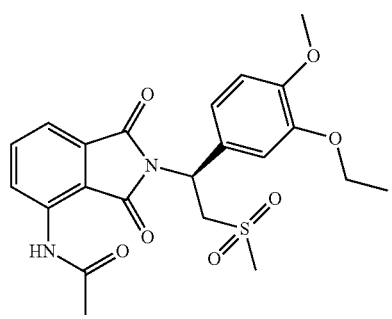

Apremilast
I

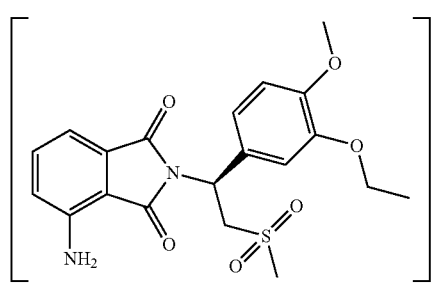

II

As used herein, "[ ]"/bracket in Scheme II indicates the intermediates (preferably intermediate of formula (II)) are not isolated in the synthesis of apremilast of formula I.

The reagents, solvents and reaction conditions employed in the one-pot process may be similar or identical to those employed in the reactions as depicted in Scheme I and as discussed above.

Suitably, the one-pot process comprises:

(1) preparing a compound (S)-4-amino-2-(1-(3-ethoxy-4-methoxyphenyl)-2-(methylsulfonyl) ethyl) isoindoline-1,3-dione (II) by protonation and cyclization of salt of (S)-1-(3-ethoxy-4-methoxyphenyl)-2methanesulfonylethylamine (III) with 3-amino phthalic acid in the presence of a protonating agent and preferably a suitable base and a suitable organic solvent at a suitable temperature; without isolating the compound/intermediate of formula (II), and (2) acetylating (S)-4-amino-2-(1-(3-ethoxy-4-methoxyphenyl)-2(methylsulfonyl)ethyl)isoindoline-1,3-dione (II) with an acetylation agent in the presence of a base preferably in a suitable solvent (the reaction mixture), to obtain apremilast.

As discussed, the compound of formula (II) is not isolated between steps (1) and (2). Instead an aqueous layer comprising the compound of formula II is separated and extracted with a suitable solvent, such as ethylacetate, butyl acetate, isopropyl acetate, acetonitrile, preferably ethylacetate.

The layer (comprising the compound of formula II and solvent) is then distilled to obtain the compound of formula (II) and this compound is then used in step (2) above.

Step (2) may further comprise isolating and drying apremilast into a solid form. Any suitable techniques known in the art may be used, for example filtering and then drying under vacuum.

Apremilast of formula (I) may then be converted to a pharmaceutically acceptable salt thereof by any suitable process known in the art.

The salt of (S)-1-(3-ethoxy-4-methoxyphenyl)-2methanesulfonylethylamine (III) may be prepared by the same or similar process as discussed previously with reference to scheme I.

The one-pot synthesis (i.e. without isolation of the intermediate II) avoids the need for lengthy separation processes such as filtration, washing and purification of the intermediates and also saves time and resources. This thus increases the chemical yield and makes the process economical and suitable for industrial scale up.

A further aspect of the present invention provides a process for preparing (S)-4-amino-2-(1-(3-ethoxy-4-methoxyphenyl)-2-(methylsulfonyl) ethyl) isoindoline-1,3-dione of formula II

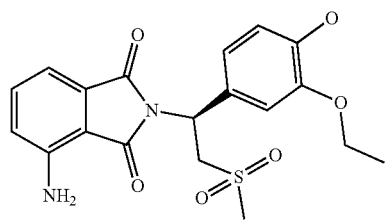

II which process comprises protonating and cyclizing a salt of (S)-1-(3-ethoxy-4-methoxyphenyl)-2-(methylsulfonyl) ethanamine of formula III

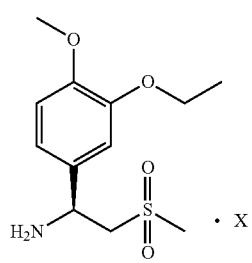

III with 3-amino phthalic acid in the presence of a protonating agent.

The reagents, solvents and reaction conditions employed in the preparation of the intermediate of formula (II) may be similar or identical to those employed in the reactions as depicted in Schemes I and 2 and as discussed above.

Still another aspect of the present invention provides a pharmaceutical composition comprising a therapeutically effective amount of pure apremilast along with one or more pharmaceutically acceptable ingredients such as carriers, excipients or diluents.

According to another aspect of the present invention, there is provided a pharmaceutical composition comprising apremilast or a pharmaceutically acceptable salt thereof, prepared by a process of the present invention as described above, together with one or more pharmaceutically acceptable excipients. Such excipients are well known to those skilled in the art.

The pharmaceutical composition comprising apremilast produced by the process of the invention along with one or more pharmaceutically acceptable ingredients may further be formulated as: solid oral dosage forms such as, but not limited to, powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the form of immediate release, delayed release or modified release.

According to a further aspect of the present invention there is also provided apremilast, or a pharmaceutically acceptable salt thereof, prepared by a process of the present invention for use in the treatment of psoriasis or psoriatic arthritis.

According to a further aspect of the present invention there is also provided use of apremilast, or a salt thereof, prepared by a process of the present invention in the manufacture of a medicament for the treatment of psoriasis or psoriatic arthritis.

According to a further aspect of the present invention there is also provided a method of treating psoriasis or psoriatic arthritis comprising administering to a patient in need thereof apremilast, or a salt thereof, prepared by a process of the present invention.

According to a further aspect of the present invention there is also provided apremilast of formula I, or a pharmaceutically acceptable salt thereof, prepared substantially as described herein with reference to the examples.

According to another aspect of the present invention there is also provided a process substantially as herein described with reference to the examples.

Certain specific aspects and embodiments of the present invention will be explained in more detail with reference to the following examples, which are provided by way of illustration only and should not be construed as limiting the scope of the invention in any manner.

EXAMPLES

Example 1: (S)-1-(3-Ethoxy-4-methoxyphenyl)-2-(methylsulfonyl)ethanamine N-acetyl-L-leucine salt (N-acetyl-L-leucine salt of Formula III) Step (I)

To a reaction mixture of 700 ml methanol and 100 grams (gm) (0.366 moles) of 1-(3-ethoxy-4-methoxy phenyl)-2-(methylsulfonyl) ethanamine, 38 gm (0.2196 moles) of N-acetyl-L-leucine was charged. The reaction mixture was heated to reflux for 1 hour. The reaction mixture was cooled to 25° C. to 30° C. and stirred for 1 hour. The product was filtered and washed with 100 ml methanol. The obtained solid material was dried under vacuum at 30° C. to obtain (S)-1-(3-ethoxy-4-methoxyphenyl)-2-(methylsulfonyl) ethanamine N-acetyl-L-leucine salt.

(Yield=68.0 gms)
R-isomer: 0.5%

Example 2: (S)-4-amino-2-(1-(3-ethoxy-4-methoxyphenyl)-2-(methylsulfonyl) ethyl) isoindoline-1,3-dione of Formula II (Step II)

Reaction mixture of 100 ml acetonitrile, 10 grams (gms) (0.0554 moles) of 3-amino phthalic acid, 15 gms (0.0336 moles) of (S)-1-(3-ethoxy-4-methoxyphenyl)-2-(methyl sulfonyl) ethanamine N-acetyl-L-leucine salt, 13.26 gms (0.221 moles) of acetic acid were stirred at 25° C. for 10 minutes. 11.16 gms (0.11 moles) of triethylamine was slowly added to the reaction mixture. The mixture was heated to reflux temperature (approximately 80° C.) and maintained for 3 hours. Solvent was completely distilled under vacuum at 45° C. Water (150 ml) was charged and stirred for 3 hour at 25° C. to 30° C. Solid was filtered and washed with water. The obtained solid material was dried under vacuum at 50° C. to obtain (S)-4-amino-2-(1-(3-ethoxy-4-methoxyphenyl)-2-(methyl sulfonyl) ethyl) isoindoline-1, 3-dione.

Yield=13.0 grams

Example 3: Preparation of Apremilast of Formula I (Step III)

To a reaction mixture of 100 ml ethyl acetate, 10 grams (gms) (0.0239 moles) (S)-4-amino-2-(1-(3-ethoxy-4-methoxyphenyl)-2-(methylsulfonyl) ethyl) isoindoline-1, 3-dione, 8.25 gms (0.0598 moles) potassium carbonate, was charged 5.6 gms (0.0717 moles) of acetyl chloride at 25° C. to 30° C. The reaction mixture was refluxed for 3 hours and monitored by thin layer chromatography (TLC). After completion of reaction, the reaction mixture was cooled to 25° C. to 30° C. The reaction mixture was extracted with water. The obtained organic layer was washed with 5% sodium chloride solution. Solvent was completely distilled under vacuum. 30 ml acetone and 60 ml ethanol was charged and stirred for 3 hours at 25° C. to 30° C. The solid was filtered and dried under vacuum to obtain apremilast.

(Yield=9.0 grams)
HPLC purity 99.3% and R-isomer 0.82%.

Example 4: Insitu Process of Preparation of Apremilast of Formula I (One-Pot Process)

Reaction mixture of 100 ml acetonitrile, 10 grams (gms) (0.0554 moles) of 3-amino phthalic acid, 15 gms (0.0336 moles) of (S)-1-(3-ethoxy-4-methoxyphenyl)-2-(methyl sulfonyl) ethanamine N-acetyl-L-leucine salt, 20 ml of acetic acid were stirred at 25° C. for 10 minutes. 20 ml of triethylamine was slowly added to the reaction mixture. The mixture was heated to reflux temperature and maintained for 3 hours. Solvent was completely distilled under vacuum below 45° C. Water (150 ml) and ethyl acetate was charged and stirred for 30 min at 25° C. to 30° C. Layers were separated and aqueous layer was extracted with ethylacetate. The combined ethyl acetate layer was distilled to obtain (S)-4-amino-2-(1-(3ethoxy-4-methoxyphenyl)-2-(methyl sulfonyl) ethyl) isoindoline-1, 3-dione. To the residue was charged acetone (150 ml) and potassium carbonate (15 grams). The reaction mass was cooled to 0° C. and slowly was charged acetyl chloride (15.0 ml) at 0° C. The reaction mixture was maintained at temperature 20° C. for 1 hour and checked for completion of reaction (by TLC). On completion of reaction, acetone was distilled. TO the residue was added water (150 ml) and ethyl acetate which was further stirred for 30 min at 25° C. to 30° C., layers were separated and aqueous layer was extracted with ethylacetate. Combined ethyl acetate layer was distilled. To the residue was added acetone and methanol, further stirred for 4 hrs and filtered. The wet cake was subjected to hot methanol slurry, further filtered and dried to obtain apremilast Yield: 11.30 grams
Purity: 99.5%

The invention claimed is:
1. A process for preparing apremilast of formula I, or a pharmaceutically acceptable salt thereof,

Formula I

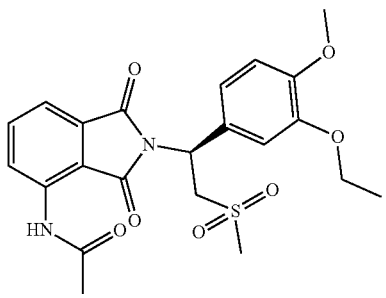

which process comprises acetylating (S)-4-amino-2-(1-(3-ethoxy-4-methoxyphenyl)-2-(methylsulfonyl) ethyl) isoindoline-1,3-dione of formula II

II

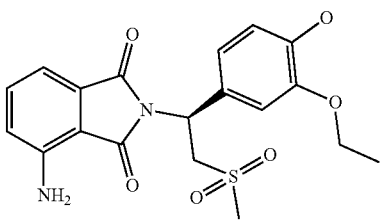

with an acetylating agent in the presence of a base to obtain apremilast of formula I; and optionally thereafter forming a pharmaceutically acceptable salt of the compound so formed,
wherein the base is an inorganic base selected from the group consisting of sodium bicarbonate, potassium bicarbonate, lithium carbonate, sodium carbonate, potassium carbonate, sodium hydroxide, potassium hydroxide or any mixture thereof.

2. The process according to claim 1, wherein the acetylating agent is selected from the group consisting of acetyl chloride, acetic acid or mixtures thereof.

3. The process according to claim 2, wherein the acetylating agent is acetyl chloride.

4. The process according to claim 1, wherein the base is potassium carbonate.

5. The process according to claim 1, wherein the acetylating step is carried out in the presence of an organic solvent.

6. The process according to claim 5, wherein the organic solvent is an aromatic hydrocarbon, a chlorinated hydrocarbon, or an ester.

7. The process according to claim 6, wherein the organic solvent is an ester.

8. The process according to claim 1, wherein the acetylating step is carried out at a temperature in the range of about 25 to 30° C.

9. The process according to claim 1, wherein the acetylating step is carried out in the absence of acetic anhydride.

10. The process according to claim 1, wherein (S)-4-amino-2-(1-(3-ethoxy-4-methoxyphenyl)-2-(methylsulfonyl) ethyl) isoindoline-1,3-dione of formula II is prepared by protonating and cyclizing a salt of (S)-1-(3-ethoxy-4-methoxyphenyl)-2-(methylsulfonyl)ethanamine of formula III

III

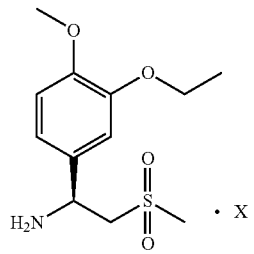

with 3-amino phthalic acid in the presence of a protonating agent.

11. The process according to claim 10, wherein the protonating agent is selected from the group consisting of mineral acids, sulphonic acids, carboxylic acids, alcohols, phenols, amines, primary or secondary amines, ammonium halides, pyridine hydrohalides and water.

12. The process according to claim 10, wherein the protonating agent is an alkane carboxylic acid or aromatic carboxylic acid.

13. The process according to claim 12, wherein the protonating agent is an alkane carboxylic acid.

14. The process according to claim 10, wherein the protonating and cyclizing step is carried out in the presence of a base.

15. The process according to claim 14, wherein the base is an organic base or an inorganic base.

16. The process according to claim 15, wherein the base is an organic base selected from the group consisting of methylamine, dimethylamine, or triethylamine.

17. The process according to claim 15, wherein the base is an inorganic base selected from the group consisting of sodium hydroxide, potassium hydroxide, sodium carbonate, potassium carbonate, sodium bicarbonate, potassium bicarbonate, sodium methoxide and potassium methoxide.

18. The process according to claim 16, wherein the base is triethylamine.

19. The process according to claim 10, wherein the protonating and cyclizing step is carried out in the presence of an organic solvent.

20. The process according to claim 19, wherein the organic solvent is selected from the group consisting of dimethylsulfoxide, N,N-dimethylformamide, N,N-dimethylacetamide, tetrahydrofuran, acetone, acetonitrile, toluene or combinations thereof.

21. The process according to claim 20, wherein the organic solvent is acetonitrile.

22. The process according to claim 10, wherein the protonating and cyclizing step is carried out at a temperature in the range of about 10° C. to about 90° C.

23. The process according to claim 10, wherein the process further comprises isolating (S)-4-amino-2-(1-(3-ethoxy-4-methoxyphenyl)-2-(methylsulfonyl) ethyl) isoindoline-1,3-dione of formula II into a solid form between the protonating and cyclizing step and the acetylating step.

24. The process according to claim 10, wherein the process does not comprise isolating (S)-4-amino-2-(1-(3-ethoxy-4-methoxyphenyl)-2-(methylsulfonyl) ethyl) isoindoline-1,3-dione of formula II between the protonating and cyclizing step and the acetylating step.

25. The process according to claim 10, wherein the salt of (S)-1-(3-ethoxy-4-methoxyphenyl)-2-(methylsulfonyl) ethanamine of formula III is prepared by reacting 1-(3-ethoxy-4-methoxyphenyl)-2-(methylsulfonyl)ethanamine of formula IV;

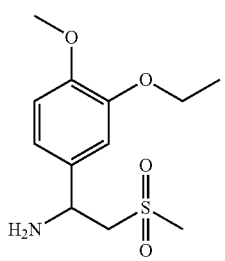

IV with a chiral resolving agent and isolating the salt of (S)-1-(3-ethoxy-4-methoxyphenyl)-2-(methylsulfonyl) ethanamine of formula III.

26. The process according to claim 25, wherein the chiral resolving agent is selected from the group consisting of tartaric acid, di-benzoyl tartaric acid, di-p-toluoyl tartaric acid, o-nitrobenzoyl tartaric acid, diacetyltartaric acid, 10-camphorsulphonic acid, 8-camphorsulphonic acid, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, N-acetyl-L-leucine, 10-camphor sulfonic acid, camphoric acid, α-bromocamphoric acid and methoxyacetic acid.

27. The process according to claim 25, wherein the chiral resolving agent is N-acetyl-L-leucine.

28. The process according to claim 1, further comprising converting the compound of formula I to a pharmaceutically acceptable salt thereof.

29. A process for preparing apremilast of formula I, or a pharmaceutically acceptable salt thereof,

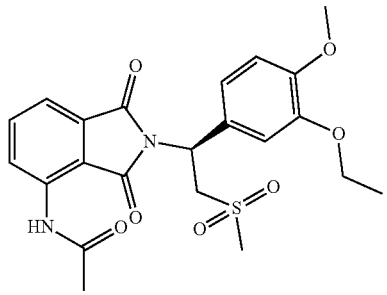

Formula I which process comprises the steps of (a) protonating and cyclizing a salt of (S)-1-(3-ethoxy-4-methoxyphenyl)-2-(methylsulfonyl)ethanamine of formula III

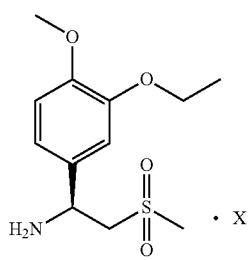

III with 3-amino phthalic acid in the presence of a protonating agent to obtain (S)-4-amino-2-(1-(3-ethoxy-4-methoxyphenyl)-2-(methylsulfonyl) ethyl) isoindoline-1,3-dione of formula II;

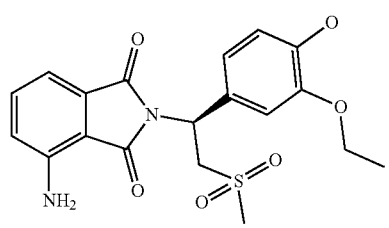

II and (b) acetylating (S)-4-amino-2-(1-(3-ethoxy-4-methoxyphenyl)-2-(methylsulfonyl) ethyl) isoindoline-1,3-dione of formula II with an acetylating agent in the presence of a base to obtain apremilast of formula I, and optionally thereafter forming a pharmaceutically acceptable salt of the compound so formed; wherein there is no isolation of (S)-4-amino-2-(1-(3-ethoxy-4-methoxyphenyl)-2-(methylsulfonyl) ethyl) isoindoline-1,3-dione of formula II between steps (a) and (b).

30. A process for preparing (S)-4-amino-2-(1-(3-ethoxy-4-methoxyphenyl)-2-(methylsulfonyl) ethyl) isoindoline-1,3-dione of formula II

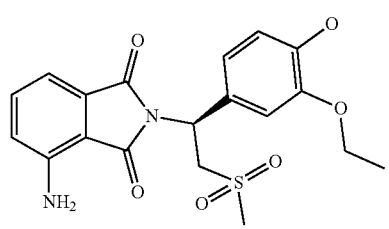

II which process comprises protonating and cyclizing a salt of (S)-1-(3-ethoxy-4-methoxyphenyl)-2-(methylsulfonyl)ethanamine of formula III

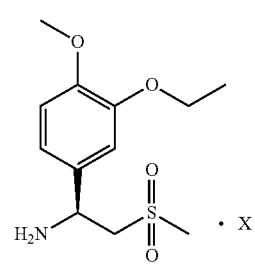

III with 3-amino phthalic acid in the presence of a protonating agent.

* * * * *